United States Patent [19]

Jon et al.

[11] 4,086,817

[45] May 2, 1978

[54] METHOD AND APPARATUS FOR DETERMINING THE ACCEPTABILITY OF A WELD FORMED BY APPLYING REPETITIVE PULSES OF ENERGY TO THE WELD SITE

[75] Inventors: Min-Chung Jon, Cranbury; Charles Andrew Keskimaki, Plainsboro, both of N.J.

[73] Assignee: Western Electric Co., Inc., New York, N.Y.

[21] Appl. No.: 813,025

[22] Filed: Jul. 5, 1977

[51] Int. Cl.² ............................................ G01N 29/00
[52] U.S. Cl. ..................................................... 73/587
[58] Field of Search ................ 73/584, 587, 588, 658, 73/88 R, 88.3; 340/248 N, 261; 228/103, 104

[56] References Cited

U.S. PATENT DOCUMENTS

| | | | |
|---|---|---|---|
| 3,824,377 | 7/1974 | Notvest | 235/92 PD |
| 3,965,726 | 6/1976 | Vahaviolos | 73/587 |
| 4,007,631 | 2/1977 | Saifi et al. | 73/587 |

*Primary Examiner*—Richard C. Queisser
*Assistant Examiner*—Stephen A. Kreitman
*Attorney, Agent, or Firm*—D. J. Kirk

[57] ABSTRACT

Stress wave emission signals emanating from a weld during an AC welding operation are detected during (1) the time when the AC power is on, (2) the post weld time period, and (3) during each half-cycle of the AC weld when the absolute magnitude of the current is decaying. The stress wave emission signals are counted in each of these periods and compared to predetermined ranges of values to determine the acceptability of the weld.

17 Claims, 6 Drawing Figures

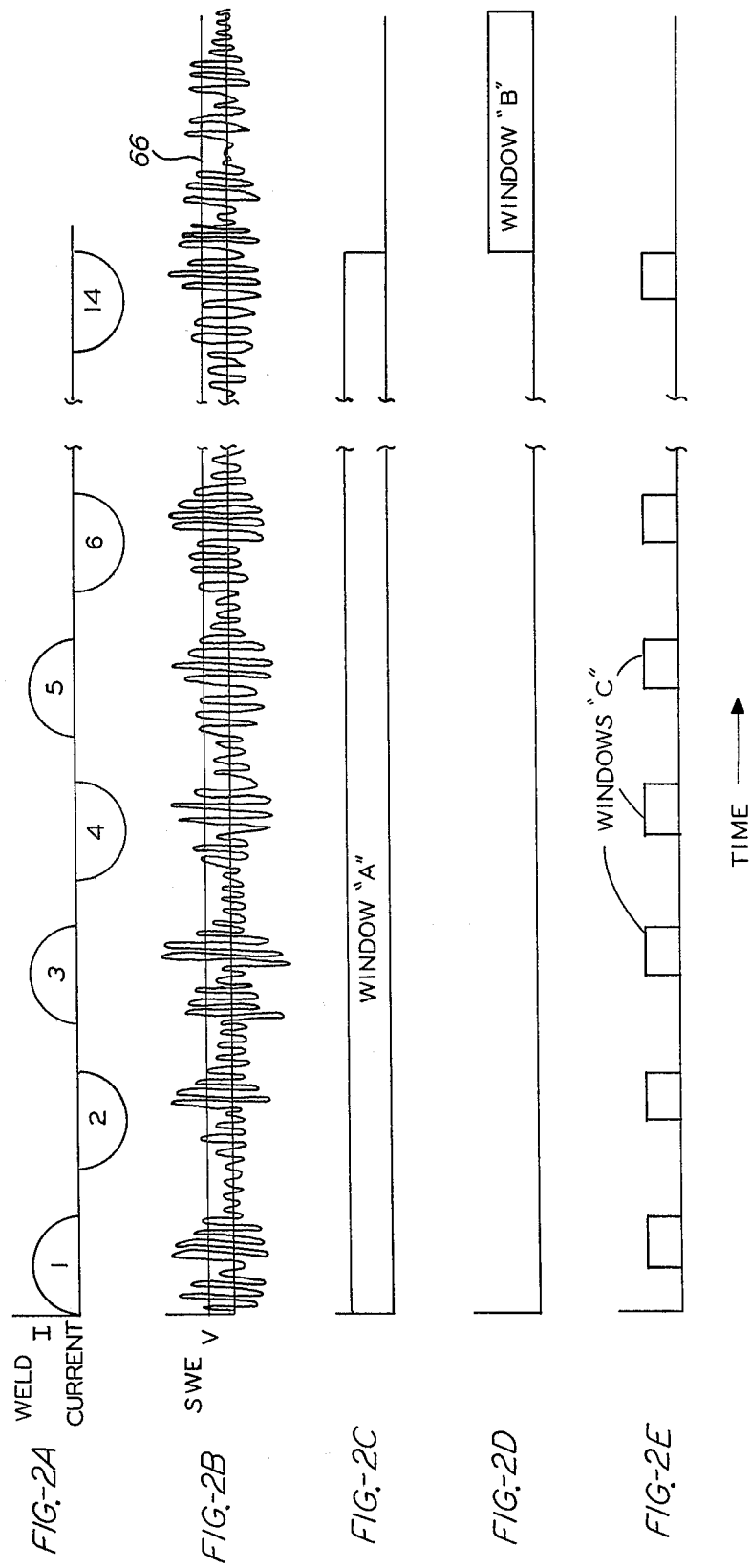

4,086,817

METHOD AND APPARATUS FOR DETERMINING THE ACCEPTABILITY OF A WELD FORMED BY APPLYING REPETITIVE PULSES OF ENERGY TO THE WELD SITE

BACKGROUND OF THE INVENTION

1. Field of the Invention

This invention relates to a method and apparatus for the real-time, non-destructive evaluation of welds formed by applying repetitive pulses of energy to the weld site. In particular, the invention is directed to monitoring stress wave emission signals during particular portions of the repetitive energy pulses to determine the acceptability of the weld.

2. Description of the Prior Art

The evaluation of adhesion bonds, welds or the like using real-time, non-destructive stress wave emission techniques is well known. For instance, U.S. Pat. No. 3,965,726 which issued on June 29, 1976 to S. J. Vahaviolos and is assigned to the instant assignee, describes the real-time evaluation of capacitive discharge welds by monitoring stress waves emitted from the weld site. Stress Wave Emissions (SWE's) may be defined as elastic waves which are characterized by low amplitude, short duration and fast rise time signals which are propagated in a structure as a result of an applied stress. As described in the aforementioned patent, the SWE energy emitted from the weld area during the solid-to-liquid phase transformation and the liquid-to-solid phase transformation are measured. The stress wave energy emitted during the liquid-to-solid phase transformation is subtracted from the stress wave energy emitted during the solid-to-liquid phase transformation and that value is compared with a predetermined value to determine the acceptability of the weld.

The foregoing technique has been found to be most successful in determining the acceptability of a weld. However, when the weld power is repetitively applied, as in AC welding, laser welding or the like, problems arise. During melting, a high SWE energy is to be expected which is reflective of the weld energy input as well as the size of the weld nugget; while during resolidification, the SWE energy should be low, which indicates few cracks and an acceptable weld. However, SWE signal energy measured during the period of application of the AC pulses in combination with the SWE signal energy measured during a predetermined time period after the AC weld energy has been applied, has been found to yield inconsistent results.

Accordingly, there is a need for real-time, non-destructive SWE techniques for determining the acceptability of a weld formed by a repetitively pulsed welding operation.

SUMMARY OF THE INVENTION

The instant method overcomes the foregoing problem of determining the acceptability of a weld which has been formed using repetitive pulses of energy by monitoring stress wave emission signals emanating from the weld. The method comprises the steps of counting and storing the number of excursions of the stress wave emission signals above a predetermined threshold during: (a) a first time period during the application of all the repetitive pulses of energy, (b) a second time period after the termination of the repetitive pulses of energy, and (c) a third time period comprised of the sum of all of the time intervals during which the absolute magnitude of each of the pulses of energy is decaying. The stored counts are then individually compared with predetermined values to provide an indication of the acceptability of the weld in each of the time periods. The weld acceptability information is combined from all of the time intervals to determine the acceptability of the weld.

In a further embodiment, counts representative of the SWE signal energy, rather than signal excursions, in each of the above time intervals may be stored and later compared with predetermined energy counts to determine the acceptability of the weld.

Advantageously, the counts representative of the SWE signal energy or the number of signal excursions for the above-referred to third time period reflect undesirable cracking occurring during the time when the current is decaying during each of the repetitive pulses. By comparing the SWE count or energy accumulated in this time interval with a predetermined value to determine the acceptability of the weld and combining this information with the weld acceptability information for the second and third time intervals, a reliable determination of the weld acceptability can be made.

BRIEF DESCRIPTION OF THE DRAWINGS

FIGS. 2A to 2E depict electrical waveforms occurring during the instant SWE signal evaluation method.

DETAILED DESCRIPTION OF THE PREFERRED EMBODIMENT

Figure 1:
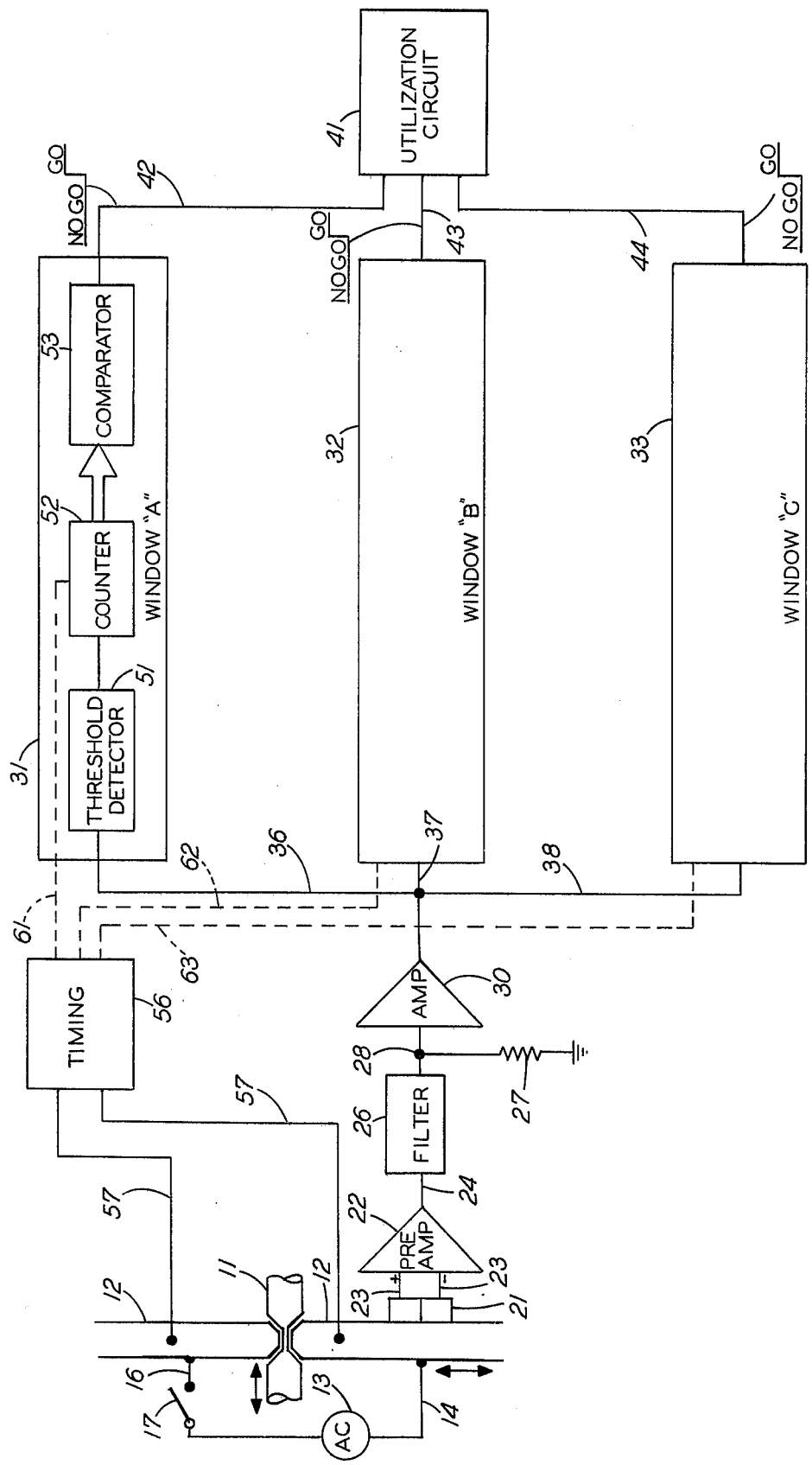
FIG. 1 is a partial block diagram of SWE apparatus used to evaluate a weld formed using repetitive pulses of energy.

The instant invention will be described in relation to the real-time, non-destructive evaluation of an AC weld. However, it will be understood that such description is exemplary only and is for the purposes of exposition and not for the purposes of limitation. It will be readily appreciated that the instant inventive concept is equally applicable to other operations involving bonding, testing or the like where repetitive energy pulses are applied to a bonding site to form or test the bond. For example, the present concepts could be implemented during a laser welding operation where the laser energy is directed at the bond site and repetitively pulsed.

Welding involves the steps of mechanically holding the articles to be welded together, melting the parts at their common interface, causing molten material co-flow, and resolidifying the molten volume. The volume where the melting occurs is generally called the molten-resolidification zone or weld nugget, while the region where grain structure modification takes place is generally referred to as the heat affected zone. The required interfacial heat can be supplied in a number of different ways, one of which is by capacitor discharge welding where a pulse of high current is passed across the weld part interface.

The aforementioned Vahaviolos patent describes techniques whereby SWE energy emanating from such single pulse weld is measured during the solid-to-liquid phase transformation and during the liquid-to-solid phase transformation periods. The SWE energy in the latter period is substracted from the SWE in the former period and that difference is compared with the predetermined value to determine the acceptability of the weld. However, such a technique when applied to a weld formed by using repetitive energy pulses has been found to yield results which are inconsistent and not subject to accurate interpretation.

The instant SWE technique for evaluating the acceptability of welds formed using repetitive energy pulses provides consistent and reliable results. In an exemplary embodiment of the invention shown in FIG. 1, a tubulation 11 which extends from a vessel (not shown) was pinch welded shut to seal the vessel from the atmosphere. However, the instant invention is not limited to the AC welding of such a tubulation, for it is contemplated that the AC welding of any articles are amenable to the instant SWE evaluation methods.

FIG. 1 shows the tubulation 11 between a pair of welding electrodes 12—12 which are connected to an alternating current power source 13 via leads 14 and 16. The lead 16 has a switch 17 therein to control the application of the current to the electrodes 12—12. A piezoelectric differential transducer 21 (hereinafter referred to as sensor 21) is shown as being mechanically coupled to one of the electrodes 12—12 but could also be coupled to the tubulation 11 or other parts of the welding apparatus as long as there is good mechanical coupling from the weld site to the sensor 21. The sensor 21 may be comprised of Barium Titanate or Lead Zirconate Titanate operating in the resonant mode of approximately 1 Mhz. Also, Lead Metaniobate sensors have been employed where relatively high sensitivity, high working temperatures and freedom from electrical ringing are desired.

The signals which are detected by the sensor 21 comprise waves which are (a) generated by other electrical components proximate the welding apparatus; (b) generated by the tubulation 11 or other articles being welded, or the sensor 21 due to non-transient factors such as temperature and strain variations; and (c) stress waves due to microcracking, comprising bulk and surface waves emanating from the weld nugget in the tubulation 11 during the weld cycle.

Whenever a phase transformation occurs in the weld nugget, energy is released in the form of mechanical stress waves, which waves, in turn excite the sensor 21. Depending on the wave dampening at the interface, the travelling mechanical stress impulses will cause the sensor 21 to provide output voltage changes which are substantially proportional to the amplitude of the impulses. Because of the low amplitude of the SWE signals, it is desirable to provide for good transmission of the mechanical stress wave and amplification of the output voltage of the sensor 21.

The sensor 21 is connected to a low-noise preamplifier 22 over a pair of leads 23—23. The preamplifier 22 should be of a design having a sensitivity which is preferably in the range of 1–4$\mu$V but can include a sensitivity beyond this range, as for example, 6$\mu$V.

The output of the preamplifier 22 is transmitted over a lead 24 to a band-pass filter 26 which has a pass band that encompasses the natural frequency of the sensor 22, but which falls outside the range of noise frequencies generated by other components proximate the system. The filter 26 is preferably a commercially available fifth order or higher, band-pass filter having a pass band from 100 Khz to 2.2 Mhz. A resistor 27 is preferably connected to a line 28 which connects the output of the filter 26 to the input of an amplifier 30 to match the impedance input thereof. The amplifier 30 advantageously has a fast slewing rate of approximately 100 V/sec., such as, for example, a commercially available model 715 operational amplifier.

The output of the amplifier 30 is connected to a plurality of SWE analyzer circuits 31, 32 and 33 over leads 36, 37 and 38, respectively. The outputs of the analyzer circuits 31, 32 and 33 are connected to a utilization circuit 41 over leads 42, 43 and 44, respectively.

As can be seen in FIG. 1, the SWE analyzer circuits 31, 32 and 33 are connected in parallel relationship and are independently operable. Only the analyzer circuit 31 is shown in detail, for analyzers 32 and 33 are comprised of the same equipment and operate in substantially the same manner. Each analyzer circuit 31, 32 or 33 is comprised of a tandem connection of a threshold detector 51, a counter 52 and a comparator 53.

A timing circuit 56 is connected across the electrodes 12—12 via leads 57—57 and provides output timing pulses in response to the activation of AC power source 13. The timing circuit 56 is individually connected to the analyzer circuits 31, 32 and 33 over leads 61, 62 and 63, respectively, shown with dashed lines.

FIG. 2A is a graphical representation of seven cycles of AC weld current with the half cycles numbered from 1 to 14. FIG. 2B is a representative SWE signal as it appears at the output of the amplifier 30. FIGS. 2C, 2D and 2E depict time windows in which the counters 51 are enabled.

In operation, the tubulation 11 is placed between the electrodes 12—12 and the electrodes moved toward each other to contact the tubulation to apply pressure thereto. As the switch 17 is closed to provide an AC current, from the power supply 13, across the terminals 12 to weld the tubulation 11 closed.

SWE signals emitted from the weld area are monitored by the sensor 21 during and after the AC weld current has been applied. The SWE signals pass through the preamplifier 22, the filter 26 and the amplifier 30 and appear as shown in FIG. 2B on leads 36, 37 and 38 at the output of the amplifier 30. The analyzer circuits 31, 32 and 33 simultaneously receive the SWE signals but operate on the signal during different time periods (or windows), as will be hereinafter set forth. The operation of analyzer 31 will be described in detail and reference will be made to the analyzers 32 and 33 to note any differences.

The SWE analyzer 31 receives the SWE signals (see FIG. 2B) at the threshold detector 51 over the lead 36 and provides an output pulse for each excursion of the signal which is above a predetermined DC threshold 66. The output pulses from the threshold detector 51 are forwarded to the counter 52 which will count and store the pulses during a preset time period of the weld cycle designated as "Window A" in FIG. 2C. The length of the Window A is controlled by an enable signal from the timing circuit 56 on lead 61. The enable signal is removed at the termination of the AC current and the count is stored in the counter 52 until the end of the post weld period at which time the SWE count is forwarded to the comparator 53. The comparator 53 will compare the SWE signal count from the counter 52 with a predetermined count above which indicates an acceptable weld and at or below which indicates that the weld is not acceptable. An output representative of a go or no-go signal will be forwarded from the comparator 53 to the utilization circuit 41 over the lead 42.

An additional advantage of the instant technique is that the counts obtained during the Window A period may be used to check the system. For if the number of counts in that time period is equal to or less than a predetermined value, then the system should be examined for low weld power, poor mechanical coupling of the SWE sensor, improper electrode pressure, or the like.

The analyzer circuits 32 and 33 operated in substantially the same manner with like apparatus. The only difference is the time period during which the SWE signals are counted and stored in counters 52. Accordingly, analyzer 32 will count SWE signal excursions above the threshold 66 during the post weld period, which is designated "Window B" in FIG. 2D upon receipt of an enable signal from the timing circuit 56 over lead 62. That count is also forwarded to a comparator 53 which compares the count to a predetermined count above which indicates an unacceptable weld and at or below which is indicative of an acceptable weld. A go or no-go signal is then forwarded to the utilization circuit.

The counter of the analyzer circuit 33 receives an enable pulse from the timing circuit 56 over the lead 63 during that portion of each half cycle of the welding current in which the absolute magnitude of the current is decreasing. Accordingly, FIG. 2E shows a plurality of "Window C's" in which the SWE signal counts are made. The counter accumulates the total count for all the Window C's and stores the count until the end of the post weld period at which time the accumulated SWE signal count is forwarded to a comparator 53 for comparison with a predetermined count above which indicates an unacceptable weld and at or below which is indicative of an acceptable weld. An output from the comparator, representing a go or no-go signal will be forwarded to the utilization circuit 41 over lead 44.

The utilization circuit 41 receives the go or no-go signals from each of the analyzer circuits 31, 32 and 33 and provides an audible and/or visual signal which indicates an acceptable weld if all the received signals are "go" and provides an audible and/or visual signal indicative of an unacceptable weld if any of the received signals are "no-go."

In a particular working embodiment of the instant SWE evaluation apparatus, the tubulation was monel metal having an inner diameter of 0.075 inch and an outer diameter of 0.127 inch and seven full cycles of weld current were applied across the terminals 12. Window A was 0.12 second in length, Window B was also 0.12 second, while each Window C was 0.002 second long, while the DC threshold voltage 66 was 0.090 volt. The predetermined counts used for comparison to the detected SWE signal excursion counts were 2,200; 200; and 200 for Window A, Window B and Window C, respectively.

Although the instant SWE signal evaluation techniques have been described in terms of counting the number of SWE signal excursions above a preset threshold occurring in particular time intervals, it should not be so limited. An alternative method of implementing the instant concept would be to measure the SWE energy emanating from the weld site rather than counting pulses. Accordingly, the SWE energy in each time interval could be determined and converted to a number of counts which are proportional to such energy as taught in the previously referred to Vahaviolos patent, which is incorporated herein by reference. The SWE energy counts in each of the time intervals would then be compared to predetermined energy count values to provide an indication of the acceptability of the weld for that time interval. The acceptability (or non-acceptability) indications from each of the intervals would than be combined, as previously described, to determine the acceptability of the weld.

What is claimed is:
1. A method of non-destructively determining, in real time, the acceptability of a weld formed by repetitive pulses of energy, wherein stress wave emission signals emanating from the weld site are monitored, the method comprising the steps of:
counting and storing the number of excursions of the stress wave emission signals above a predetermined threshold during:
(a) a first time period during the application of all the repetitive pulses of energy;
(b) a second time period after the termination of the last of the repetitive pulses; and
(c) a third time period comprised of the sum of all of the time intervals during which the absolute magnitude of each of the repetitive pulses is decaying;
comparing the stored counts with predetermined values to provide an indication of the acceptability of the weld in each of the time periods; and
combining the indication of acceptability from all of the comparing means to determine the acceptability of the weld.

2. The method as set forth in claim 1 wherein the count made in each of the time intervals is representative of the stress wave energy emitted from the weld site during the respective time intervals.

3. The method as set forth in claim 1 wherein the repetitive pulses of energy are provided by an AC welder.

4. The method as set forth in claim 1 wherein the repetitive pulses of energy are provided by a pulsed laser.

5. The method as set forth in claim 1 wherein the stored count of the first time period is compared to a predetermined value above which is indicative of an acceptable weld and at or below which indicates an unacceptable weld.

6. The method as set forth in claim 1 wherein the stored count of the second time period is compared to a predetermined value above which is indicative of an unacceptable weld and at or below which indicates an acceptable weld.

7. The method as set forth in claim 1 wherein the stored count of the third time period is comared to a predetermined value above which is indicative of an unacceptable weld and at or below which indicates an acceptable weld.

8. The method as set forth in claim 1 wherein in the combining step all the indications determined by the comparing step must be acceptable for the weld to be considered acceptable.

9. An apparatus for non-destructively determining, in real time, the acceptability of a weld formed by repetitive pulses of energy, wherein stress wave emission signals emanating from the weld site are monitored, the apparatus being comprised of the combination of:
means for counting and storing the number of excursions of the stress wave emission signals above a predetermined threshold during:
(a) a first time period during the application of all the repetitive pulses of energy;
(b) a second time period after the termination of the last of the repetitive pulses; and
(c) a third time period comprised of the sum of all of the time intervals during which the absolute magnitude of each of the repetitive pulses is decaying;

means for comparing the stored counts with predetermined values to provide an indication of the acceptability of the weld in each of the time periods; and means for combining the indication of acceptability from all of the comparing means to determine the acceptability of the weld.

10. An apparatus as set forth in claim 9 wherein the count made in each of the time intervals is representative of the stress wave energy emitted from the weld site during the respective time intervals.

11. The apparatus as set forth in claim 9 wherein the repetitive pulses of energy are provided by an AC welder.

12. The apparatus as set forth in claim 9 wherein the repetitive pulses of energy are provided by a pulsed laser.

13. The apparatus as set forth in claim 9 wherein the stored count of the first time period is compared to a predetermined value above which is indicative of an acceptable weld and at or below which indicates an unacceptable weld.

14. The apparatus as set forth in claim 9 wherein the stored count of the second time period is compared to a predetermined value above which is indicative of an unacceptable weld and at or below which indicates an acceptable weld.

15. The apparatus as set forth in claim 9 wherein the stored count of the third time period is compared to a predetermined value above which is indicative of an unacceptable weld and at or below which indicates an acceptable weld.

16. The apparatus as set forth in claim 9 wherein the indications received by the combining means from all of the comparing means must be acceptable for the weld to be considered acceptable.

17. An apparatus for non-destructively determining, in real time, the acceptability of an AC weld wherein stress wave emission signals emanating from the weld site are monitored, the apparatus being comprised of the combination of:

a sensor mounted proximate the weld site to sense the stress wave emission signals emanating from the weld;

an amplifier, to amplify the stress wave emission signal output from the sensor;

a first, a second and a third stress wave emission signal analyzer connected electrically in a parallel relationship to simultaneously receive the stress wave emission signals from the amplifier;

each of the stress wave emission signal analyzers being comprised of:

a threshold detector to detect each excursion of the stress wave emission signals that are above a preset threshold;

a counter to count and accumulate pulses from the threshold detector, each pulse being representative of an excursion of the stress wave emission signal passing above the threshold; and a comparator to compare the accumulated count from the counter with a predetermined count to provide an indication of the acceptability of the weld;

the first signal analyzer accumulates a count during a first time window encompassing the application of all of the AC pulses;

the second signal analyzer accumulates a count during a second time period after the termination of the last of the AC pulses;

the third signal analyzer accumulates a count during a third time period comprised of the sum of all of the time intervals during which the absolute magnitude of each of the AC pulses is decaying; and a utilization circuit for combining the indication of acceptability from all of the time intervals to determine the acceptability of the weld.

* * * * *